US012734288B2

(12) United States Patent
Carstens et al.

(10) Patent No.: US 12,734,288 B2
(45) Date of Patent: Sep. 15, 2026

(54) METHOD FOR DETERMINING THE COMPLIANCE OF A CAVITY OF ELASTIC MEDICAL PRODUCTS FOR LEAKAGE

(71) Applicant: Novanta Medicine GmbH, Berlin (DE)

(72) Inventors: Jan-Hendrik Carstens, Berlin (DE); Ibrahim Ilik, Bielefeld (DE); Felix Menzel, Berlin (DE)

(73) Assignee: Novanta Medical GmbH, Berlin (DE)

( * ) Notice: Subject to any disclaimer, the term of this patent is extended or adjusted under 35 U.S.C. 154(b) by 438 days.

(21) Appl. No.: 18/008,223

(22) PCT Filed: Jun. 7, 2021

(86) PCT No.: PCT/DE2021/000107

§ 371 (c)(1),
(2) Date: Dec. 21, 2022

(87) PCT Pub. No.: WO2021/244691

PCT Pub. Date: Dec. 9, 2021

(65) Prior Publication Data

US 2023/0241307 A1 Aug. 3, 2023

(30) Foreign Application Priority Data

Jun. 5, 2020 (DE) ........................ 102020003418.7

(51) Int. Cl.
*A61M 5/142* (2006.01)

(52) U.S. Cl.
CPC ..... *A61M 5/142* (2013.01); *A61B 2562/0247* (2013.01)

(58) Field of Classification Search
None
See application file for complete search history.

(56) References Cited

U.S. PATENT DOCUMENTS

| | | | | |
|---|---|---|---|---|
| 5,629,871 | A | 5/1997 | Love et al. | |
| 10,194,813 | B2 * | 2/2019 | Bharucha | A61B 5/42 |
| 2010/0236555 | A1 | 9/2010 | Jafari et al. | |
| 2017/0160175 | A1 | 6/2017 | Al-Mayah | |
| 2022/0218928 | A1 * | 7/2022 | Liu | A61M 16/024 |
| 2023/0270954 | A1 * | 8/2023 | Carstens | A61B 5/02007 604/503 |

FOREIGN PATENT DOCUMENTS

| | | | |
|---|---|---|---|
| DE | 4309380 | A1 | 9/1994 |
| DE | 19809867 | C1 | 9/1999 |

(Continued)

OTHER PUBLICATIONS

Tautorat, Balloon-Based Measuring System for Compliance Investigations, In: Current Directions in Biomedical Engineering, 4 (1), 2018, pp. 539-542.

(Continued)

*Primary Examiner* — Peter J Macchiarolo
*Assistant Examiner* — Jermaine L Jenkins
(74) *Attorney, Agent, or Firm* — McCarter & English, LLP; David J. Silvia

(57) ABSTRACT

The invention relates to a method for determining cavity volumes of rubber-elastic medical products (e.g., latex products) for destruction-free leakage testing and to devices for carrying out said method.

4 Claims, 10 Drawing Sheets

(56) References Cited

FOREIGN PATENT DOCUMENTS

Figure 2:
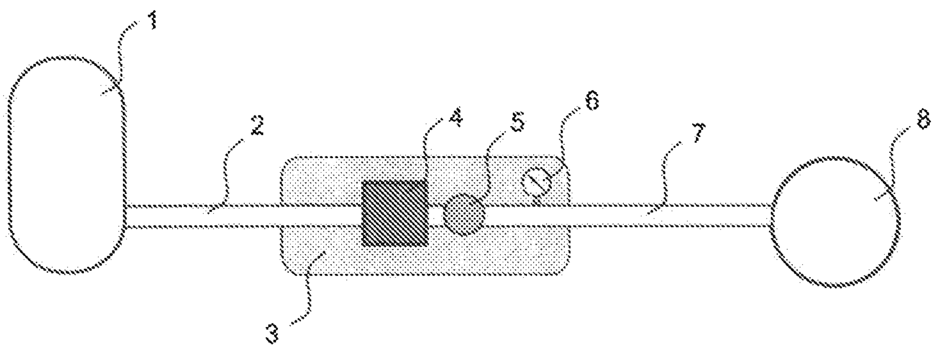
Figure 3:
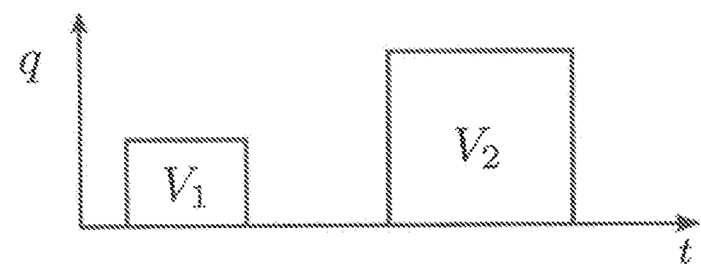
Figure 3:
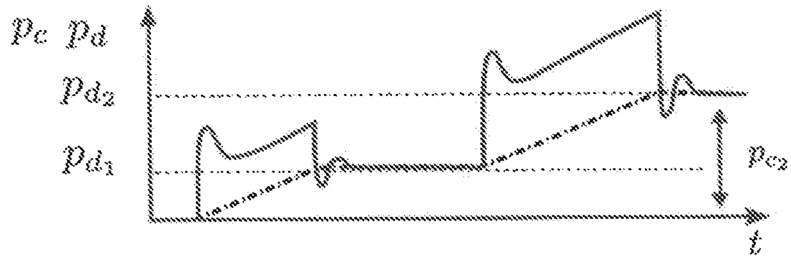

| | | |
|---|---|---|
| JP | 2012512697 A | 6/2012 |
| JP | 2020509918 A | 4/2020 |

OTHER PUBLICATIONS

Examination Report Excerpt of Priority DE 102020003418.7 (no date).

PCT International Search Report dated Sep. 27, 2021 for PCT/DE2021/000107.

Office Action from related Japanese patent application No. 2022-574750 dated Apr. 1, 2025.

* cited by examiner

Figure 1a

Figure 1b

METHOD FOR DETERMINING THE COMPLIANCE OF A CAVITY OF ELASTIC MEDICAL PRODUCTS FOR LEAKAGE

SUBJECT MATTER OF THE INVENTION

The invention relates to a method for determining the compliance of a cavity of rubber-elastic medical products (e.g., latex products) for destruction-free leakage testing and to devices for carrying out said method.

PRIOR ART

Rubber-elastic medical products (such as, e.g., rubber gloves, balloon catheters, condoms, etc.) are subjected to a multitude of tests before placing them on the market. Faults of homogeneity are looked for, but perforation and burst tests are also carried out. For testing rubber-elastic medical products, they are normally filled with gas or liquid. Depending on the size of the thus formed hollow space (cavity), the volume of a fluid necessary therefor (e.g., $N_2$, $CO_2$, water, saline solution) varies, in order to expand the product so far that a test for production errors, in particular for leakages, will be enabled.

In the case of gaseous fluids (such as, e.g., $CO_2$), devices are used that adjust, by using pressure reducers, the necessary volumetric flow, which is then supplied into the medical product.

The situation is different when using liquid fluids (such as, e.g., saline solutions). Here, e.g., peristaltic pumps are used that are able to vary the volumetric flow via the control of the pump rotation.

By introducing the volumetric flow into the cavity, the hollow space is filled with the fluid, and the pressure in this cavity increases. At the same time, the hollow space of the medical product expands.

The so-called compliance (expansibility) of a cavity $C_c$ can be determined using the relationship between volume $V_c$ and resulting pressure $p_c$, as a static characteristic using the equation $$C_c=V_c/p_c$$

Figures 1A, 1B:
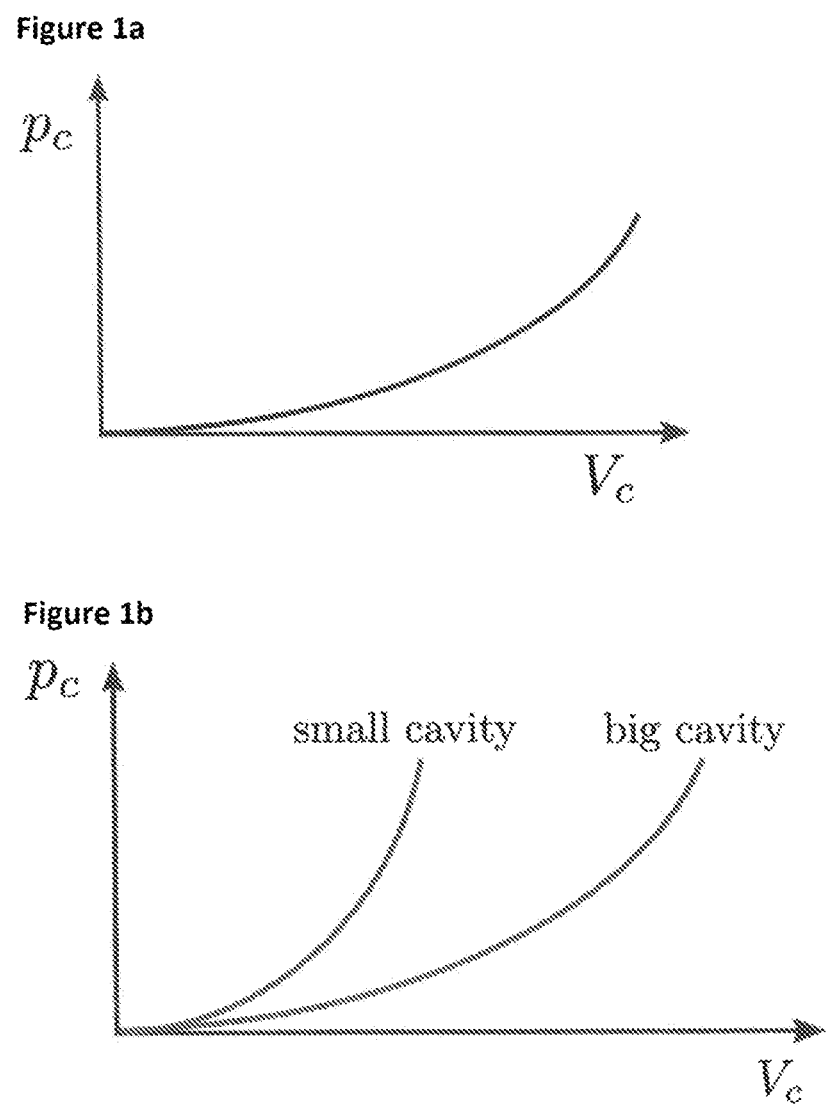

(see FIG. 1*a*).

The reciprocal of the compliance Cc is referred to as elasticity $E_c=1/C_c$.

Here, the basic condition is that the specific pressure in this cavity must not have any harmful effects on the medical product (with the exception of burst tests, in which the destruction of the product is intended). For this reason, pressure sensors are typically used for determining the cavity pressure. By a suitable regulation, the necessary volumetric flow can be calculated, without a product-damaging cavity pressure being caused. Accordingly, the necessary volumetric flow is realized by the regulation of the pressure reducer or the peristaltic pump. However, it must be taken into account that during the fluid supply, the pressure is not measured: For the pressure measurement, the fluid supply is interrupted for a short time, in order to establish a pressure equilibrium, which represents the actual pressure in the medical product. After the measurement, the fluid supply is continued.

Depending on the medical product and its size, a significant variation of the necessary volume is required, in order to inflate the rubber-elastic product to the desired pressure (see FIG. 1*b*).

Actually, thus, the user of the test device needs to perform a multitude of necessary settings, in order to communicate the information about the product and its size to the device. In the context of quality assurance measures, often a few products are taken from a product series and subjected to corresponding expansion or burst tests on a separate test rig. The manual input of the individual product parameters (e.g., type and size of the product) may lead to faults. The same applies to the production of small batches.

Therefrom can be derived, in particular, the parameters and limit values for the control/regulation of the device. E.g., data sets are thus loaded, which quantify the maximum allowable flow rate of the fluid.

When the product is larger than originally assumed, then the expansion of the product takes a very long time, and undesired delays in the measurement will result. When, however, the product is smaller than originally assumed, then possibly very quickly pressures are achieved, which may lead to product damages.

In case the user sets at the test device a faulty product and its size (e.g., by preselection of a faulty glove size or selection of balloon catheter in place of glove) (adult or child), a faulty behavior of the device may result.

The prior art devices and methods are not able, up to now, to solve the described problems. The relevant prior art comprises the documents US 2007/0083126 A1, US 2010/0236555 A1, DE 4309380 A1, DE 19809867 C1, Tautorat, C. et al., Balloon-based measuring systems for compliance investigations. In: Current Directions in Biomedical Engineering 4 (1), 2018.

There is therefore a need for a regulation system of a medical-technical device that automatically determines the crucial characteristics of a cavity.

SOLUTION ACCORDING TO THE INVENTION

The present invention discloses a technical device for supplying a fluid into a rubber-elastic medical product, which device automatically determines the characteristics of a cavity and thus necessary operating parameters.

FIG. 2 shows a medical-technical device (3) according to the invention for supplying fluids, comprising the following components:

- A fluid reservoir (1), from which the fluid is taken and supplied to the supply unit (4) using a connecting element (2). The fluid may be a gas (e.g., $CO_2$ or $N_2$) or a liquid (e.g., saline solution).
- A regulated pump (actuator or supply unit) (4) for supplying the fluid in a regulated manner.
- A measuring device for the volumetric flow (5).
- A pressure sensor (6) for determining the dynamic and static pressure of the fluid.
- A connecting element (7) (e.g., tube) for supplying the fluid from the device to the medical product (8).
- An electronic storage element (not explicitly shown}, which serves for detecting measurement data. Further, an electronic computing unit (e.g., microcontroller) for sending necessary control commands to the actuators, evaluating data, loading/writing parameter data sets from the storage element.

By means of a medical-technical device comprising the said components, the compliance of the cavity can automatically be determined using the values of volumetric flow and pressure so that operating errors of the staff are avoided. To this end, different methods of determination can be applied, which are described in the following.

Method I.a

First, the rubber-elastic medical product is connected using a connecting element (fluid line) to the device. Then, the device is turned on. Before initially applying a volumetric flow, the device identifies the pressure in the cavity. Then, a predefined temporal volumetric flow q is generated using the actuator (e.g., a pulsed volumetric flow, with a defined length in time). The volumetric flow generates a pressure increase $q_c$ in the cavity.

The volume V can be determined by the integration of the volumetric flow by the measurement unit. After the defined volumetric flow, the device stops the supply and identifies the static pressure in the cavity. Thus, the elasticity can be determined using the partial pressure increase ($dp_c/dV_c$). This procedure can be repeated until a desired reference pressure in the cavity is achieved. From the partial pressure increases, then the so-called p-V diagram can be derived. This diagram, thus, provides information about the size of the cavity, i.e., the size of the medical product. Then, by comparison to system parameters, the parameterization and selection of optimum system parameters (e.g., maximum flow rate, control, and regulation parameters) can be performed. By an optional confirmation by the user, the automatic cavity detection can be confirmed.

Figure 4:
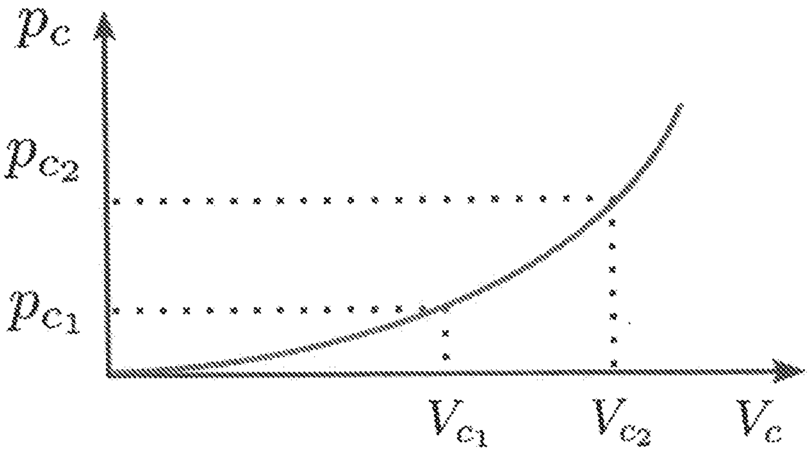
Figure 5:
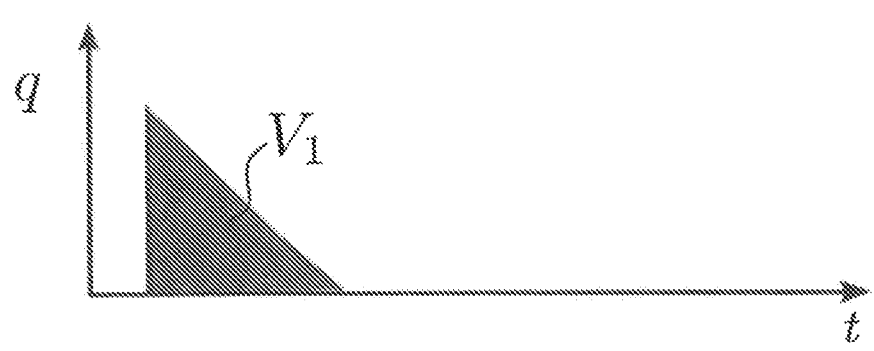
Figure 5:
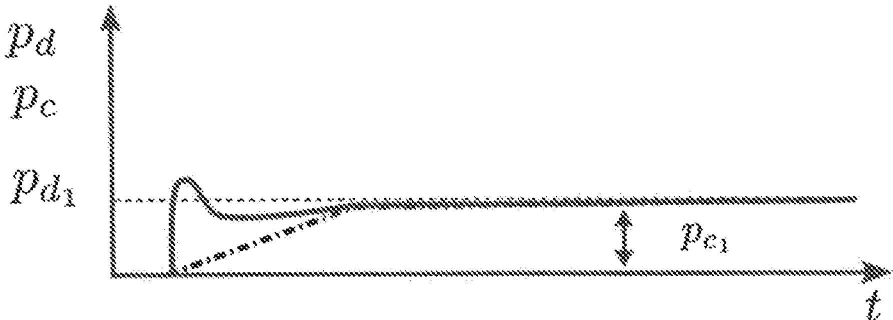
Figure 6:
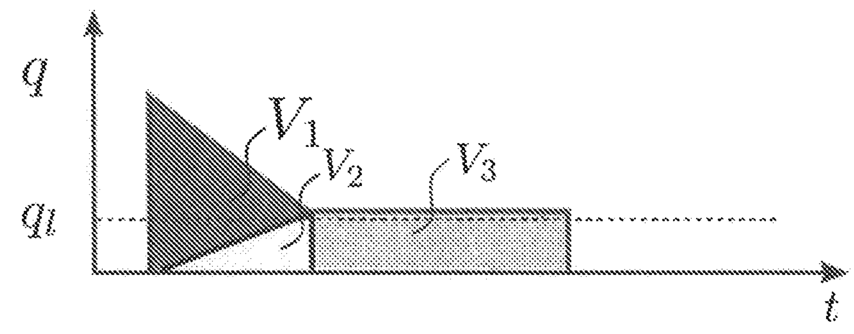
Figure 6:
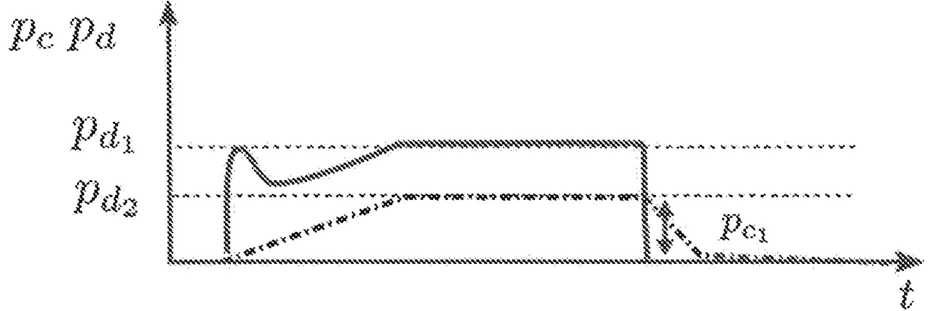
Figure 7:
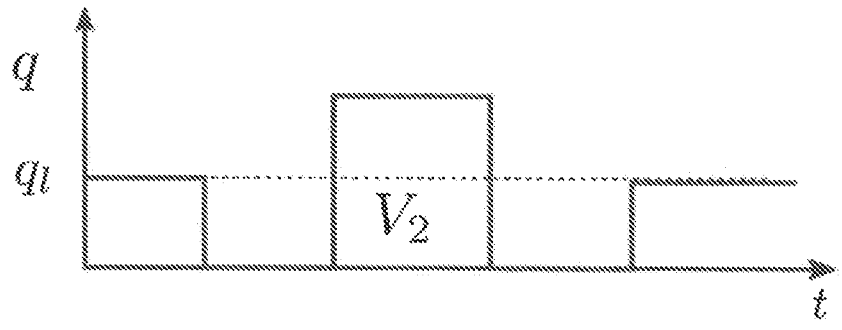
Figure 7:
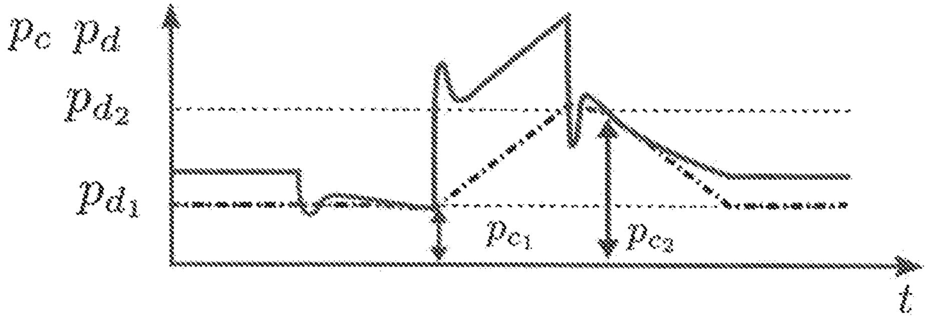

In FIG. 4, an example of this method is shown. Two volumes $V_1$ and $V_2$ are supplied temporally offset into the hollow space. Then, the pressure in the cavity p increases, and the pressure of the cavity can be determined using the pressure sensor $p_d$. This results in the working points $V_{c1}=V_1$, $p_{c1}=p_{d1}$ and $V_{c2}=V_2+V_1$, $p_{c2}=p_{d2}$. By, e.g., linear approximation, then an approximation of the p-V diagram can be calculated (see FIG. 4). The "transient response" of the pressure measurement signal at the starting point and at the stopping point of the volumetric flow can clearly be seen in the measurement diagram (FIGS. 5 to 7 bottom).

Method I.b

In the reality of product manufacture, there are sometimes leakages in the cavities. Such leakages falsify the procedure in Method I.a due to this fluid outflow of an unknown quantity. In order to compensate for the influence of the leakage in the measurement data, Method I.a is extended as follows:

By a pressure regulation device, a pressure is generated in the cavity. In this case, the volumetric flow necessary for achieving the desired pressure is predefined. In a closed cavity—without leakage—, the pressure regulation device would regulate the volumetric flow to zero when the desired pressure is achieved (see FIG. 6).

With an existing leakage in the medical product, the pressure regulation system would permanently adjust a volumetric flow, in order to compensate for the leakage. This volumetric flow, which is necessary for maintaining the pressure, is the leakage volumetric flow $q_1$ at the present cavity pressure. This is exemplarily shown in FIG. 7. Therefrom, the volumes $V^2$ and $V_3$, which leave the medical product through the leakage, can be determined. Then, the introduced volume can be cleared from the leakage.

The pressure in the cavity $p_{c1}$ at the time when the volumetric flow is stopped can be determined or approximated through prior knowledge of the pressure drop across the connecting element and the measured pressure $p_{d1}$. At this time is $p_d \approx p_{c1}$.

Herein, the evaluation can be applied as in Method I.a. In order to allow for several working points for the calculation of the p-V diagram, the reference pressure can be increased (temporarily).

By repetition for other reference pressure values, different working points of the p-V diagram and thus the cavity size can be determined.

Method II

Figure 8:
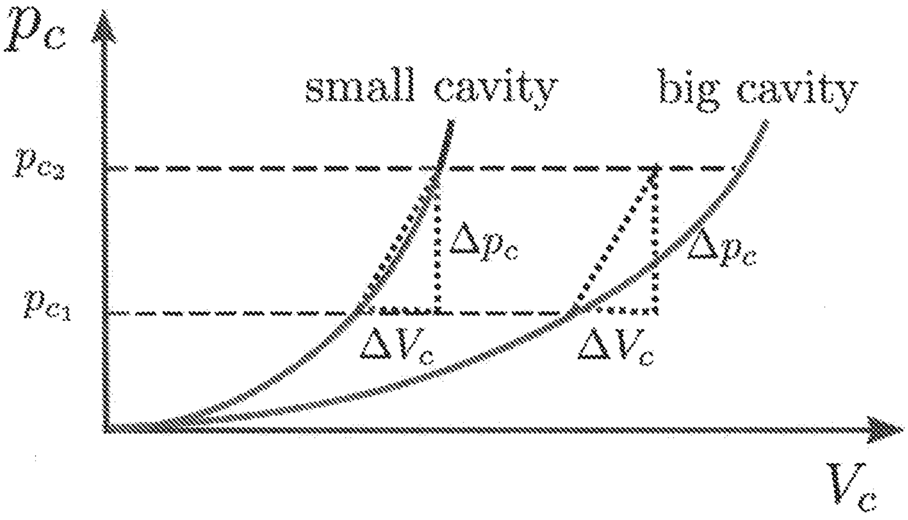

During the operation of the device, the actual working point in the p-V diagram of the medical product can be determined. A low partial capacity value ($\Delta C_c=\Delta V_c/\Delta p_c$) suggests a large product, or a large value suggests a small product. In order to obtain this information, a measurement pause is generated during the operation of the device. Herein, the volumetric flow rate is briefly interrupted, and the stationary cavity pressure $p_{c1}$ is identified. Then, a predefined temporal volumetric flow is generated using the actuator (e.g., a pulsed volumetric flow with a defined length in time). The volumetric flow generates a pressure increase in the cavity. The volume $V_2$ supplied in this period can be determined by the integration of the volumetric flow by the measurement unit. After the defined volumetric flow, the device stops the supply and identifies the static pressure in the cavity $p_{c2}$. Then, the device resumes its normal functionality (see FIG. 7). From the measurements results $\Delta C_c=V_2/(p_{c2}-p_{c1})$ . Different from Method I is that no complete information about the cavity size or the p-V diagram is known. Thus, this information only applies to the actual working point of the volumetric flow, which is necessary for maintaining the cavity pressure. However, in this working point, the plausibility for the selected default setting by the user and actually determined characteristic values can be adjusted (see FIG. 8). In the case of a discrepancy, thus, the device can automatically adjust the parameter set of the device, in order to allow the user an optimum system setup for carrying out the intervention.

This method is in particular suitable for testing balloon catheters. Depending on the application, balloon catheters may comprise openings, which represent a leakage. By means of the presented method, measurements of the compliance $C_c(C_c=V_c/p_c)$ can be carried out, in spite of the openings. Furthermore, burst tests (or tear tests) can be carried out.

Method III

During the operation of the device, the pressure is temporarily increased. To this end, an active pressure control/regulation is used. The necessary additional volume for obtaining the desired pressure in the cavity is determined in the phase of the pressure increase. Therefrom, the partial capacity value ($\Delta C=\Delta V/\Delta p$) can be determined. This is identical to the procedure in Method II. However, Method III can also be used in the initial filling phase of the cavity. To this end, the desired reference pressure of the pressure regulation is increased quasi-stationarily (very slowly in time or step-by-step). A measurement pause is not necessary with the present system parameters for the device and the connecting unit between the device and the medical product. The data of the volume and the generated pressure can thus be transferred into a p-V diagram. This provides, same as in Method I, the basis for deriving the cavity size or product type. Thus, the possibility to perform a parameterization and selection of optimum system parameters (e.g., maximum flow rate, control, and regulation parameters) will result. By an optional confirmation by the user, the automatic cavity detection can be confirmed.

Method IV

Figure 9:
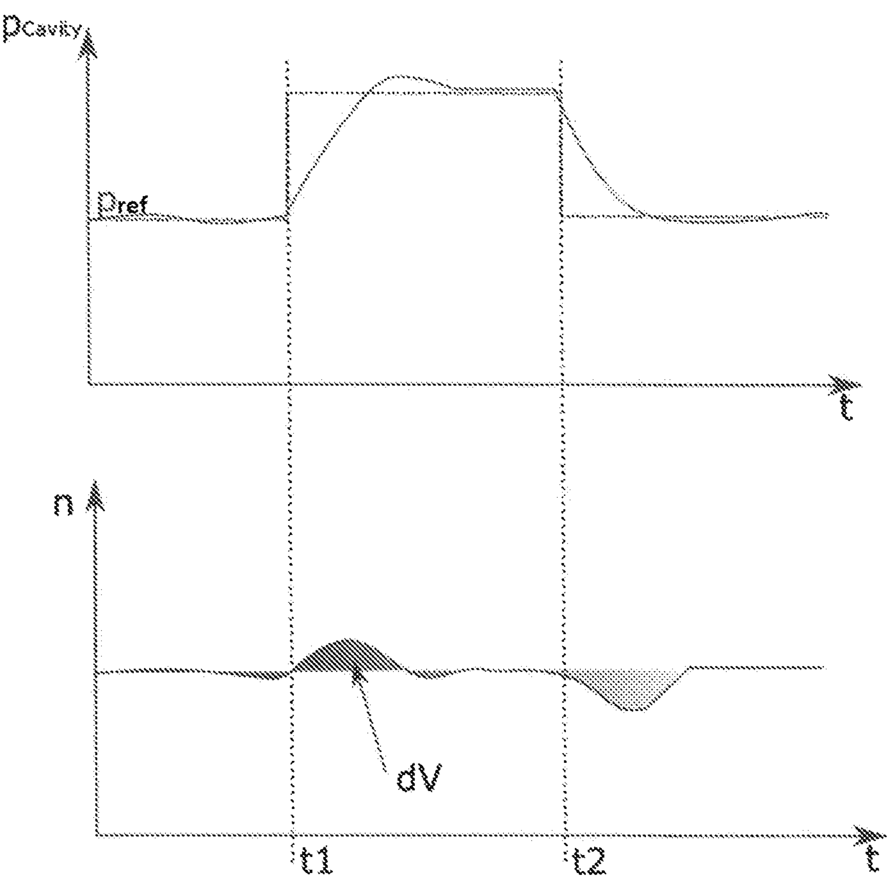
Figure 10:
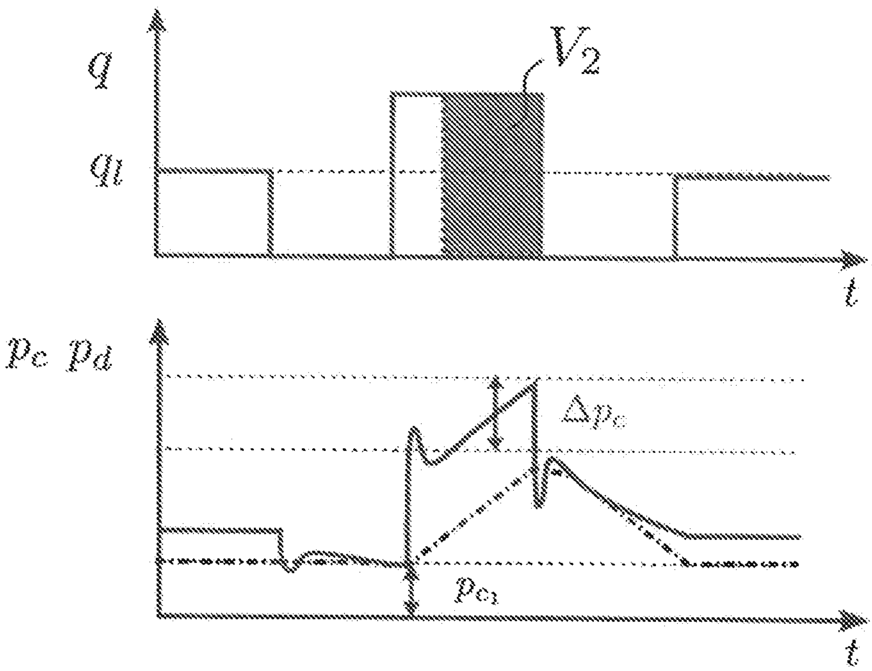

In a variation of Method II, the volumetric flow is increased after the determination of the actual cavity pressure $p_{c1}$. The rising pressure at the sensor correlates with the pressure rise in the cavity (see FIG. 9). Therefrom results that a measurement of the cavity pressure $p_{c2}$ is not necessary (comp. Method II). Instead (see FIG. 10), the increase $\Delta p_c$ relative to the volume $V_2$ is identified. After the determination of the values, the device resumes the previous operation.

Figure 11:
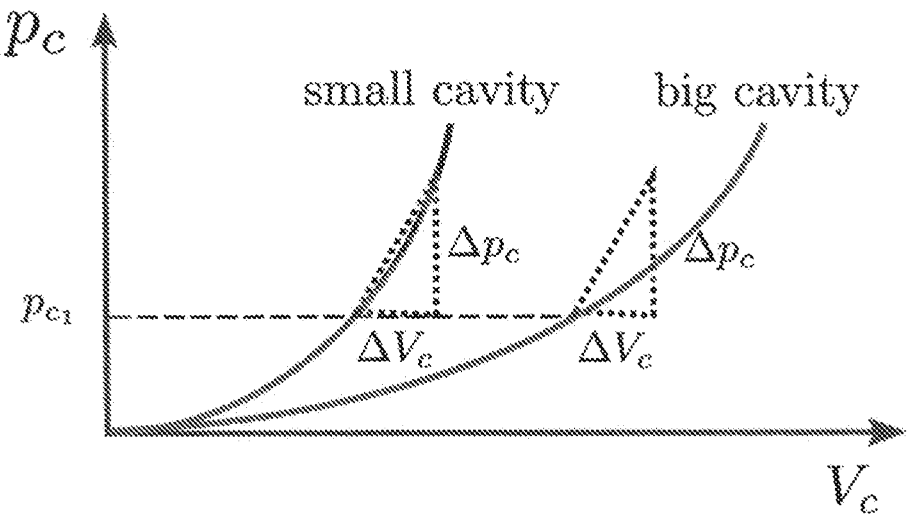

In contrast to Method II, thus, it lacks the exact knowledge of the value of the cavity pressure $p_{c2}$, however, the same partial increases will result, and thus, the value can be used by the user for comparison of the parameter set of the device to the determined cavity values (FIG. 11) and be modified if necessary, in order to guarantee an optimum parameterization of the device.

LIST OF REFERENCES (1) fluid reservoir
(2) fluid connection (supply tube of the fluid between reservoir and medical-technical device for supplying a fluid (3)
(3) medical-technical device for supplying fluids
(4) supply device
(S) measuring device for the volumetric flow of the fluid
(6) pressure sensor
(7) fluid connection
(8) rubber-elastic medical product

The invention claimed is:

1. A method for determining compliance of a cavity $C_e$ of a rubber elastic medical product using a medical-technical device, the device comprising:
at least one fluid reservoir,
at least one connecting element for supplying a fluid from the reservoir
at least one regulated pump (actuator or supply unit) (4) for supplying the fluid in a regulated manner,
at least one measuring device (5) for measuring a volumetric flow of the fluid,
at least one pressure sensor (6) for determining a dynamic and static pressure of the fluid,
at least one electronic storage element for detecting measurement data, and
at least one electronic computing unit (e.g., microcontroller)
the method comprising the following steps performed by the electronic computing unit controlling the device:
a) controlling the regulated pump (4) to introduce the fluid into the cavity
b) receiving, from the measuring device (5) and the pressure sensor (6), single of multiple measurements of the volume of the fluid introduced into the cavity and of the cavity pressure resulting therefrom, and
c) calculation of the compliance of the cavity $C_c$ using the equation $C_c=V_c/p_c$.

2. The method for determining compliance of a cavity according to claim 1, characterized by a temporally offset introduction of at least two defined fluid volumes into the cavity and consequent calculation of a partial pressure increase $(dp_c/dV_c)$.

3. The method for determining compliance of a cavity according to claim 1, characterized by the determination of a leakage volumetric flow $q_1$ before the single or multiple measurements of the volume introduced into the cavity and of the cavity pressure resulting therefrom and by taking into account the leakage volumetric flow $q_1$ when calculating $C_c$ using the equation $(\Delta C_c=(\Delta V_c-q_1)/\Delta p_c)$.

4. A device for determining compliance of a cavity $C_c$ of a rubber-elastic medical product, comprising at least one fluid reservoir (1), from which a fluid is taken,
at least one regulated pump (actuator or supply unit) (4) for supplying the fluid in a regulated manner,
at least one measuring device (5) for a volumetric flow of the fluid,
at least one pressure sensor (6) for determining a dynamic and static pressure of the fluid,
at least one connecting element (7) (e.g., tube) for supplying the fluid from the device to the cavity (8),
at least one electronic storage element, which serves for detecting measurement data,
at least one electronic computing unit (e.g., microcontroller), wherein the at least one electronic computing unit is configured to: a) supply control commands to the regulated pump (4) to introduce the fluid into the cavity. b) receive, from the measuring device (5) and the pressure sensor (6), single or multiple measurements of the volume of the fluid introduced into the cavity and of the cavity pressure resulting therefrom, and c) calculate the compliance of the cavity $C_c$ using the equation $C_c=V_c/p_c$.

* * * * *